United States Patent [19]
Matson et al.

[11] Patent Number: 4,956,507
[45] Date of Patent: Sep. 11, 1990

[54] PROCESS FOR PREPARING 4,4'-DIFLUOROBIPHENYL

[75] Inventors: Michael S. Matson, Bartlesville, Okla.; Raymond L. Cobb, Maretta, Ohio

[73] Assignee: Phillips Petroleum Company, Bartlesville, Okla.

[21] Appl. No.: 431,244

[22] Filed: Nov. 3, 1989

[51] Int. Cl.$^5$ .................. C07C 17/26; C07C 25/18
[52] U.S. Cl. ..................................................... 570/140
[58] Field of Search ......................................... 570/140

[56] References Cited

U.S. PATENT DOCUMENTS 3,046,313 7/1962 Pummer et al. ............... 570/140
4,775,764 10/1988 Dummitt ........................ 570/140

Primary Examiner—J. E. Evans
Attorney, Agent, or Firm—Laney, Dougherty, Hessin & Beavers

[57] ABSTRACT

An improved process for preparing high yields of 4,4'-difluorobiphenyl comprised of reacting a p-halofluorobenzene Grignard reagent with a p-halofluorobenzene coupling reagent in the presence of a palladium chloride triphenylphosphine catalyst.

15 Claims, No Drawings

PROCESS FOR PREPARING 4,4'-DIFLUOROBIPHENYL

BACKGROUND OF THE INVENTION

1. Field of the Invention.

The present invention relates to a process for preparing 4,4'-difluorobiphenyl, and more particularly, to an improved such process wherein a high yield of 4,4'-difluorobiphenyl is realized.

2. Description of the Prior Art.

Because of their outstanding chemical, heat and electrical insulation resistance as well as their superior rigidity when compared to other thermoplastics, poly(arylene sulfide) resins have found favor for forming reinforced plastic composites.

A poly(arylene sulfide) resin which has been found to have a very high melting point and to be particularly suitable for use at high temperatures is comprised of biphenylene sulfide polymer. Poly(biphenylene sulfide) resin retains its hardness at temperatures as high as about 700° F. and, in addition, has a high retention of mechanical properties at elevated temperatures.

Heretofore, poly(biphenylene sulfide) resin has been prepared from sodium sulfide and 4,4'-dichlorobiphenyl. Recently, however, as a result of 4,4'-dichlorobiphenyl having been found to be hazardous to the environment and to human health, poly(biphenylene sulfide) resin has been prepared with sodium sulfide and 4,4'-difluorobiphenyl.

4,4'-difluorobiphenyl has heretofore been prepared by a process utilizing a Grignard coupling reaction. In accordance with the prior process, p-halofluorobenzene is reacted with magnesium in a solvent to form halomagnesiumfluorobenzene, the Grignard reagent. The Grignard reagent is then reacted with additional p-halofluorobenzene (the coupling reagent) in the presence of a catalyst comprised of palladium chloride or palladium supported on charcoal. This prior process results in a yield of about 80% 4-4'-difluorobiphenyl when the Grignard reagent is formed from pbromofluorobenzene and the coupling reagent is p-iodofluorobenzene. In addition, about 8% of a difluoroterphenyl byproduct is formed in the reaction. Thus, the heretofore utilized process produces a relatively low yield of 4,4'-difluorobiphenyl. In addition, the process is disadvantageous in that p-iodofluorobenzene is expensive, and a high molar ratio of the palladium chloride or palladium/charcoal catalyst is required. While p-bromofluorobenzene is much less expensive than p-iodofluorobenzene, when p-bromofluorobenzene is substituted for p-iodofluorobenzene in the coupling reaction, a very low yield of 4,4'-difluorobiphenyl is obtained.

Thus, there is a need for an improved process for preparing 4,4'-difluorobiphenyl which produces a high yield, which requires a lower quantity of catalyst and which, if desired, can utilize only less expensive p-bromofluorobenzene starting materials.

SUMMARY OF THE INVENTION

The present invention meets the needs mentioned above by providing an improved process for preparing 4,4'-difluorobiphenyl which can utilize only p-bromofluorobenzene starting materials for forming the Grignard reagent and as the coupling reagent. Further, the process of the present invention requires a relatively low catalyst loading and produces a high yield of 4,4'-difluorobiphenyl.

The improved process of this invention comprises the steps of reacting p-halofluorobenzene with magnesium in a solvent to form a halomagnesiumfluorobenzene Grignard reagent followed by reacting the Grignard reagent with additional p-halofluorobenzene in the solution in the presence of a palladium chloride triphenylphosphine coupling reaction catalyst for a time period sufficient to form a high yield of 4,4'-difluorobiphenyl. The p-halofluorobenzene can be selected from the group consisting of p-bromofluorobenzene, p-chlorofluorobenzene and p-iodofluorobenzene, with p-bromoand p-iodofluorobenzene being more preferred than p-chlorofluorobenzene. If desired, one of such p-halofluorobenzene compounds can be utilized to form the Grignard reagent with another of such compounds being utilized as the p-halofluorobenzene coupling reagent. Presently, it is preferred that the less expensive p-bromofluorobenzene be utilized both in forming the Grignard reagent and as the coupling reagent.

The palladium chloride triphenylphosphine coupling reaction catalyst which is also known by the name bis(triphenylphosphine) palladium(II) chloride brings about the production of a high yield of 4,4'-difluorobiphenyl in a time period in the range of from about 0.5 hours to about 10.0 hours at a molar ratio of Grignard reagent to catalyst in the range of from about 400 to about 15,000.

It is, therefore, a general object of the present invention to provide an improved process for preparing 4,4'-difluorobiphenyl.

A further object of the present invention is the provision of an improved process for preparing 4,4'-difluorobiphenyl which produces a high yield and utilizes less catalyst.

Yet a further object of the present invention is the provision of a process for preparing a high yield of 4,4'difluorobiphenyl from p-bromofluorobenzene starting materials.

Other and further objects, features and advantages of the present invention will be readily apparent to those skilled in the art upon a reading of the description of preferred embodiments which follows.

DESCRIPTION OF PREFERRED EMBODIMENTS

The process of the present invention utilizes a catalyzed Grignard coupling reaction for the preparation of 4,4'-difluorobiphenyl from p-halofluorobenzene starting materials. The 4,4'-difluorobiphenyl is useful as a reactant in the production of poly(biphenylene sulfide) resin as described above, as an antiseptic and as a starting material for producing other compounds.

In accordance with the process of the present invention a p-halofluorobenzene compound is reacted with magnesium in a solvent to form a halomagnesiumfluorobenzene Grignard reagent. The Grignard reagent is then reacted with additional p-halofluorobenzene in the solution in the presence of a palladium chloride triphenylphosphine catalyst to form a high yield of 4,4'-difluorobiphenyl. The palladium chloride triphenylphosphine catalyst is also known by the name of bis(triphenylphosphine) palladium(II) chloride, and is commercially available from, for example, Aldrich Chemical Company of Milwaukee, Wis.

The p-halofluorobenzene utilized to form the Grignard reagent and the additional p-halofluorobenzene reacted therewith can be the same or different and can be selected from the group consisting of p-chlorofluorobenzene, p-bromofluorobenzene and p-iodofluorobenzene. Of these, p-bromofluorobenzene is presently preferred because of its substantially lower cost.

Various solvents can be utilized for carrying out the Grignard reaction. In general, dialkylethers and cyclic ethers are suitable. A particularly suitable dialkylether is diethylether and a particularly suitable cyclic ether is tetrahydrofuran. The most preferred solvent is tetrahydrofuran.

In carrying out the first reaction to produce the halomagnesiumfluorobenzene Grignard reagent, equal molar quantities of the p-halofluorobenzene utilized and magnesium, i.e., a 1:1 mole ratio, are dispersed in the solvent used. The p-halofluorobenzene and magnesium are reacted at a temperature in the range of from about 30° C. to about 90° C., preferably from about 50° C. to about 90° C. and most preferably from about 70° C. to about 80° C. After an initial time period of from about 0.5 hours to about 5.0 hours, the additional p-halofluorobenzene and catalyst are added to the solution. The ensuing second coupling reaction is continued at the above mentioned temperature for a time period in the range of from about 0.5 hours to about 10.0 hours, preferably from about 1.0 hours to about 3.0 hours. The solid 4,4'-difluorobiphenyl produced is separated from the solvent and from unreacted and by-product materials using techniques known to those skilled in the art.

As mentioned above, the palladium chloride triphenylphosphine catalyst brings about a high yield of 4,4'-difluorobiphenyl, i.e., a yield above 90%. The molar ratio of Grignard reagent to catalyst required is in the range of from about 400 to about 15,000, preferably in the range of from about 3000 to about 10,000.

Thus, the process of the present invention results in a high yield using a low quantity of catalyst regardless of the particular p-halofluorobenzene starting materials utilized. This is contrasted with prior processes which utilize high quantities of catalyst and produce low yields.

In order to further illustrate the process of the present invention, the following example is given.

EXAMPLE

In an appropriate flask fitted with a mechanical stirrer, a thermometer, an addition flask, a reflux condenser and a connection for purging with an inert gas, various quantities of Grignard reagents were produced and reacted with various quantities of various coupling reagents in the presence of palladium chloride catalyst and palladium chloride triphenylphosphine catalyst [bis(triphenylphosphine) palladium(II) chloride]. In carrying out each of the reactions, an appropriate quantity of tetrahydrofuran solvent was added to the flask along with a crystal of iodine (to help promote the Grignard reaction). Magnesium metal was also added to the flask as well as p-bromofluorobenzene in equal molar quantities after heating a smaller quantity of the p-bromofluorobenzene with the magnesium, etc. to a temperature of about 30° C. to initiate the reaction (as evidenced by the disappearance of the iodine color). After all the p-bromofluorobenzene was added, the reaction temperature was allowed to rise to reflux temperature and continued for a short time. The catalyst was added, and then the coupling reagent used was added to the flask over an additional time period. After the addition was complete, the reaction was maintained at reflux for an additional time period. The product was recovered and the yield determined.

The palladium chloride triphenylphosphine catalyst used was prepared by reacting 30.1 g PdCl$_2$ with 94 g triphenylphosphine in the presence of 14.5 g LiCl and 300 cc methanol. The reaction mixture was stirred and heated for about 30 minutes. The reaction mixture was then allowed to stand over night at room temperature, methanol was added to the mixture, and the suspended yellow solid particles of the reaction product, PdCl$_2$(P$\phi_3$)2, were recovered from the mixture by filtration. The filter cake was washed with methanol and dried. 118.7 g of dry PdCl$_2$(P$\phi_3$)2 was obtained.

The results of these tests are given in the table set forth below.

| Run | Grignard Reagent Type | Qnty., moles | Coupling Reagent Type | Qnty., moles | Catalyst Type | Qnty., molar ratio[1] | Reaction Time, hrs. | Yield, % | Coupling Byproducts terphenyl, % | fluorophenyl, % | Unreacted Materials, % |
|---|---|---|---|---|---|---|---|---|---|---|---|
| 1 | Br$\phi$F[2] | 0.156 | I$\phi$F[3] | 0.159 | PdCl$_2$[4] | 506 | 3.5 | 80.2 | 8.14 | 4.44 | 4.35 |
| 2 | Br$\phi$F | 0.142 | Br$\phi$F | 0.145 | PdCl$_2$ | 465 | 5.0 | <5.0 | — | — | — |
| 3 | Br$\phi$F | 0.618 | Br$\phi$F | 0.619 | PdCl$_2$(P$\phi_3$)$_2$[5] | 2410 | 3.0 | 92.7 | 0.31 | 2.56 | 2.88 |
| 4 | Br$\phi$F | 1.961 | I$\phi$F | 1.946 | PdCl$_2$(P$\phi_3$)$_2$ | 4830 | 2.5 | 93.9 | 0.56 | 1.96 | 1.05 |

[1]molar ratio of Grignard Reagent to catalyst
[2]Br$\phi$F = p-bromofluorobenzene
[3]I$\phi$F = p-iodofluorobenzene
[4]PdCl$_2$ = Palladium chloride
[5]PdCl$_2$(P$\phi_3$)$_2$ = Palladium Chloride Triphenylphosphine From the table it can be seen that the process of the present invention results in significantly higher yields of 4,4'-difluorobiphenyl utilizing a much lower quantity of catalyst. Furthermore, the process of the present invention produces a high yield of 4,4'-difluorobiphenyl when the less expensive p-bromofluorobenzene is utilized in the coupling reaction step instead of the presently expensive p-iodofluorobenzene.

We claim:

1. An improved process for preparing 4,4'-difluorobiphenyl comprising the steps of:
   reacting p-halofluorobenzene with magnesium in a solvent to form a halomagnesiumfluorobenzene Grignard reagent; and then
   reacting said Grignard reagent with additional p-halofluorobenzene in said solution in the presence of a palladium chloride triphenyl-phosphine catalyst for a time period sufficient to form a high yield of said 4,4'-di-fluorobiphenyl.

2. The process of claim 1 wherein said p-halofluorobenzene is selected from the group consisting of p-bromofluorobenzene, p-chlorofluorobenzene and p-iodofluorobenzene.

3. The process of claim 1 wherein said solvent is selected from the group consisting of dialkylethers and cyclic ethers.

4. The process of claim 2 wherein said solvent is tetrahydrofuran.

5. The process of claim 1 wherein said p-halofluorobenzene is selected from p-bromofluorobenzene and p-iodofluorobenzene.

6. The process of claim 4 wherein said p-halofluorobenzene used to form said Grignard reagent and said additional p-halofluorobenzene are both p-bromofluorobenzene.

7. The process of claim 1 wherein said reactions are carried out at a temperature in the range of from about 30° C. to about 90° C.

8. The process of claim 7 wherein said reaction between said Grignard reagent and said additional p-halofluorobenzene is carried out for a time period in the range of from about 0.5 hours to about 10.0 hours.

9. An improved process for preparing 4,4'-difluorobiphenyl comprising the steps of:

reacting p-bromofluorobenzene with magnesium in a solvent to form a bromomagnesiumfluorobenzene Grignard reagent; and then reacting said Grignard reagent with a p-halofluorobenzene coupling reagent selected from the group consisting of p-bromofluorobenzene and p-iodofluorobenzene in the presence of a palladium chloride triphenylphosphine catalyst for a time sufficient to form a high yield of 4,4'-difluorobiphenyl.

10. The process of claim 9 wherein said solvent is selected from the group consisting of dialkylethers and cyclic ethers.

11. The process of claim 9 wherein said solvent is tetrahydrofuran.

12. The process of claim 9 wherein said p-halofluorobenzene coupling reagent is p-bromofluorobenzene.

13. The process of claim 9 wherein said reactions are carried out at a temperature in the range of from about 50° C. to about 90° C.

14. The process of claim 13 wherein said reaction between said Grignard reagent and said p-bromofluorobenzene coupling reagent is carried out for a time period in the range of from about 1.0 hours to about 3.0 hours.

15. The process of claim 14 wherein the molar ratio of said Grignard reagent to said catalyst is in the range of from about 3000 to about 10,000.

* * * * *